United States Patent

Hamid

[19]

[11] Patent Number: 5,851,143
[45] Date of Patent: Dec. 22, 1998

[54] DISK DRIVE TEST CHAMBER

[75] Inventor: Lotfizadeh S. Hamid, Fremont, Calif.

[73] Assignee: Thermal Industries, San Jose, Calif.

[21] Appl. No.: 644,534

[22] Filed: May 10, 1996

[51] Int. Cl.[6] .................................................... B08B 15/02
[52] U.S. Cl. ............................ 454/57; 312/236; 454/236
[58] Field of Search ................................ 454/57, 58, 187,
454/228, 229, 236; 34/213, 215, 225; 312/236,
116, 118

[56] References Cited

U.S. PATENT DOCUMENTS

| 1,745,375 | 2/1930 | Mueller | 34/213 X |
| 3,261,650 | 7/1966 | Stromqvist | 312/236 |
| 3,366,432 | 1/1968 | Carmer | 312/236 |
| 4,888,549 | 12/1989 | Wilson et al. | 324/73 R |

FOREIGN PATENT DOCUMENTS 3-284505  12/1991  Japan ..................................... 454/187

OTHER PUBLICATIONS

Lotfizadeh, H., *Phoenix 500 Disk Drive Burn–In Tester*, (Apr. 1996) San Jose, California, Advertising Material.

*Primary Examiner*—Harold Joyce

*Attorney, Agent, or Firm*—Hopkins & Carley

[57] ABSTRACT

A disk drive test chamber creates an environment for disk drives to be tested with an air circulation system that provides an even flow of air over each drive for equivalence in testing conditions. One method of providing equivalent air circulation is to have turning vanes inside air ducts to divert equal amounts of air over each shelf holding disk drives through identically sized apertures. The second method is to have apertures of varying sizes of 40, 50 and 70 percent opening per square inch in the air ducts to divert equal amounts of air. The temperature is maintained within ¼° C. of the set point by a controller through a system of heaters, air pumps, air ducts, insulation, vents, a motorized damper and an exhaust fan. The heater generates heat to simulate the actual heat of running conditions of disk drives. The pumps send air up the side air ducts and down the center air duct. The chamber has two safety features to prevent damage to the disk drives from over temperature. Four separate techniques are employed to minimize vibration to the disk drives being tested; a steel frame, a rubber air duct transition, and neoprene pads on the brackets holding the shelves and on the leveling feet.

8 Claims, 10 Drawing Sheets

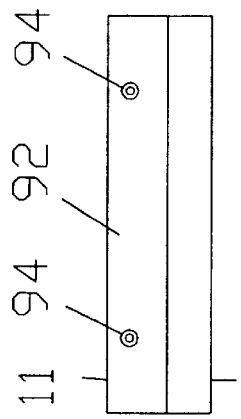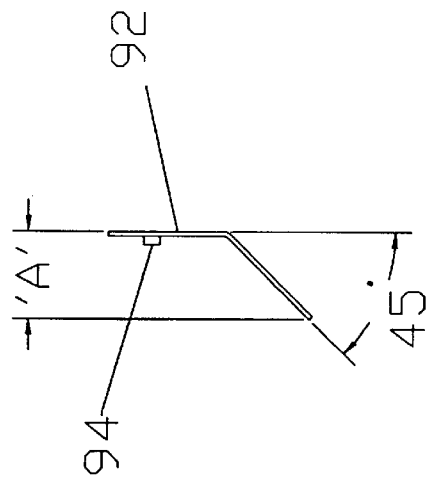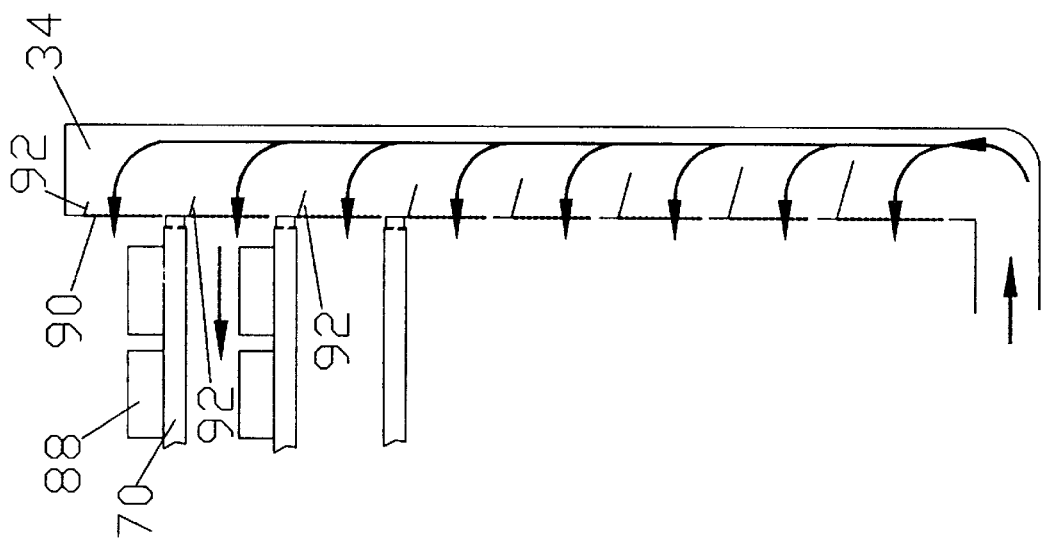

DISK DRIVE TEST CHAMBER

BACKGROUND OF THE INVENTION

1. Field of the Invention

This invention relates to a device for testing disk drives and more particularly to a chamber having consistent temperature and minimized vibrations for testing a large number of disk drives simultaneously.

2. Previous Art

Disk drive manufacturers require strict requirements from disk drive testers. Minimum temperature fluctuations are critical for accurate test conditions and for safety of the disk drives. Additionally, the latest generations of disk drives, with higher capacities, faster rotational speeds and smaller head clearance, are more sensitive to vibration. Excess vibration can affect the reliability of test results and the integrity of electrical connections. Under test conditions, the drives themselves can propagate vibrations through shelves and fixtures to adjacent units. This vibration "cross-talking," together with external sources of vibration, contributes to bump errors, head slap and NRRO. The result is lower yields and increased manufacturing costs without any real improvement in product quality.

Current test chambers are inadequate because temperature variations within the testing area can be as much as 15°–20° C. These chambers do not have safety features to automatically shut off the power to the test chamber if the temperature inside reaches levels that damage the disk drives. There is no insulation to help stabilize the temperature.

The test chambers employ multiple fans for circulating the air around the disk drives in an effort to uniformly distribute the warm air. However, the fans not only inadequately distribute the heat, they increase vibrations in the chamber.

Current test chambers are also made of sheet metal. Sheet metal lacks solidity, therefore each motor in the chamber increases the vibration to the disk drives.

What is needed is a device which minimizes temperature fluctuations within the chamber.

What is also needed is a device with minimized vibration to reduce unnecessary scrap and rework of the disk drives.

SUMMARY OF THE INVENTION

The present invention substantially reduces or overcomes all of the above problems associated with the prior art. The invention is a disk drive test chamber that controls the temperature within ¼° C. of the set point, provides equivalent air flow over each disk drive and effectively dampens vibrations.

The disk drive test chamber creates an environment for disk drives to be tested with an air circulation system that provides an even flow of air over each drive for equivalence in testing conditions. Therefore, any combination of partial loading of disk drives into the DUT bays will get even temperature airflow because each shelf has the equivalent amount of air flow at all times.

The chamber is approximately six feet high, ten feet wide and four feet deep. Two "Device Under Test" (DUT) bays are housed in the upper front part of the chamber. The back part of the chamber is an electronics control bay. Below the DUT bays is an appliance bay.

Parts related to one DUT bay are mirror images of the parts related to the other DUT bay. The left wall of the left DUT bay is covered by a side air duct and the right wall of the right DUT bay is covered by a side air duct. Each DUT bay employs a plurality of brackets for supporting shelves for holding the disk drives. Each DUT bay has a glass door, and employs a heater and an air pump located in the appliance bay for pumping air into the DUT bay.

Four separate techniques are employed to minimize vibration to the disk drives being tested, 1) the chamber is made of a steel frame for stabilizing the entire chamber, 2) vibration dampeners are attached to each shelf mounting channel on each bracket, 3) air duct transitions act as dampeners between the air pumps and the side air ducts, and 4) the adjustable leveling feet have vibration pads.

A critical aspect of the design of the invention is to ensure that an equivalent amount of air is circulated over each shelf. One method of providing equivalent air circulation is to have turning vanes inside the air ducts to divert the air over each shelf through identically sized apertures. The second method is to have apertures of varying sizes of 40, 50 and 70 percent opening per square inch in the air ducts without the use of turning vanes. The first method is preferred for mass production of the disk drive test chamber, however, each method picks up a certain amount of air and directs an equivalent flow over each shelf.

The temperature is maintained through a system of heaters, air pumps, air ducts, insulation, vents and an exhaust fan. Each of these electrical components is regulated by a controller. An operator sets the controller temperature to a desired set point. The heater generates heat to simulate the actual heat of running conditions of disk drives. The pumps send air up the side air ducts and down the center air duct. Carefully designed apertures and turning vanes in the air duct cover panels attached over the air ducts send an even air flow over each drive in the testing bay. The air is recirculated in a closed loop system and the testing bay is insulated to assist in maintaining the heat.

When the temperature in the DUT bays nears the set point, the temperature controller activates the motorized damper in the appliance bay to bring in fresh air from the front air intake vents in the lower front panel of the chamber. The motorized damper sends the fresh air through the pumps to be circulated through the DUT bays. The controller also turns on the exhaust fan on top of the chamber to expel the hot air from the chamber. In this manner, the temperature does not vary more than ¼° C. from the set point and the maximum temperature difference between the disk drives in the chamber is within the range of 3°–5° C.

The chamber has two safety features. First, the controller shuts off the heating circuit if the temperature reaches 5° C. above the set point.

The second safety feature flashes a warning and automatically shuts off electrical power to the entire system if the temperature reaches 7° C. above the set point.

Accordingly, it is an object of the present invention to provide a disk drive test chamber that effectively dampens vibrations.

It is a further object of the present invention to provide a disk drive test chamber having a consistent temperature inside the DUT bays.

It is a further object of the present invention to provide equivalent air flow over each disk drive.

Other objects and further scope of applicability of the present invention will become apparent from the detailed description given below. It should be understood, however, that this detailed description, while indicating preferred embodiments of the invention, is given by way of illustration only, since various changes and modifications within the spirit and scope of the invention will become apparent to those skilled in the art.

It is an advantage of this invention to provide a device that maintains a controlled temperature, provides equivalent air flow over each disk drive and effectively dampens vibrations.

BRIEF DESCRIPTION OF THE DRAWING

For a further understanding of the objects and advantages of the present invention, two embodiments are described in the following detailed description with reference to the accompanying figures, in which like parts are given like reference numerals and wherein:

FIG. 9 is a cross-sectional view of a side air duct having an air duct cover panel through the line 9—9 of FIG. 8 and illustrating the turning vanes on the inside of the air duct cover panels.

FIG. 10 is a front view of a turning vane.

FIG. 11 is a side view of a turning vane.

DETAILED DESCRIPTION OF THE INVENTION

Figure 1:
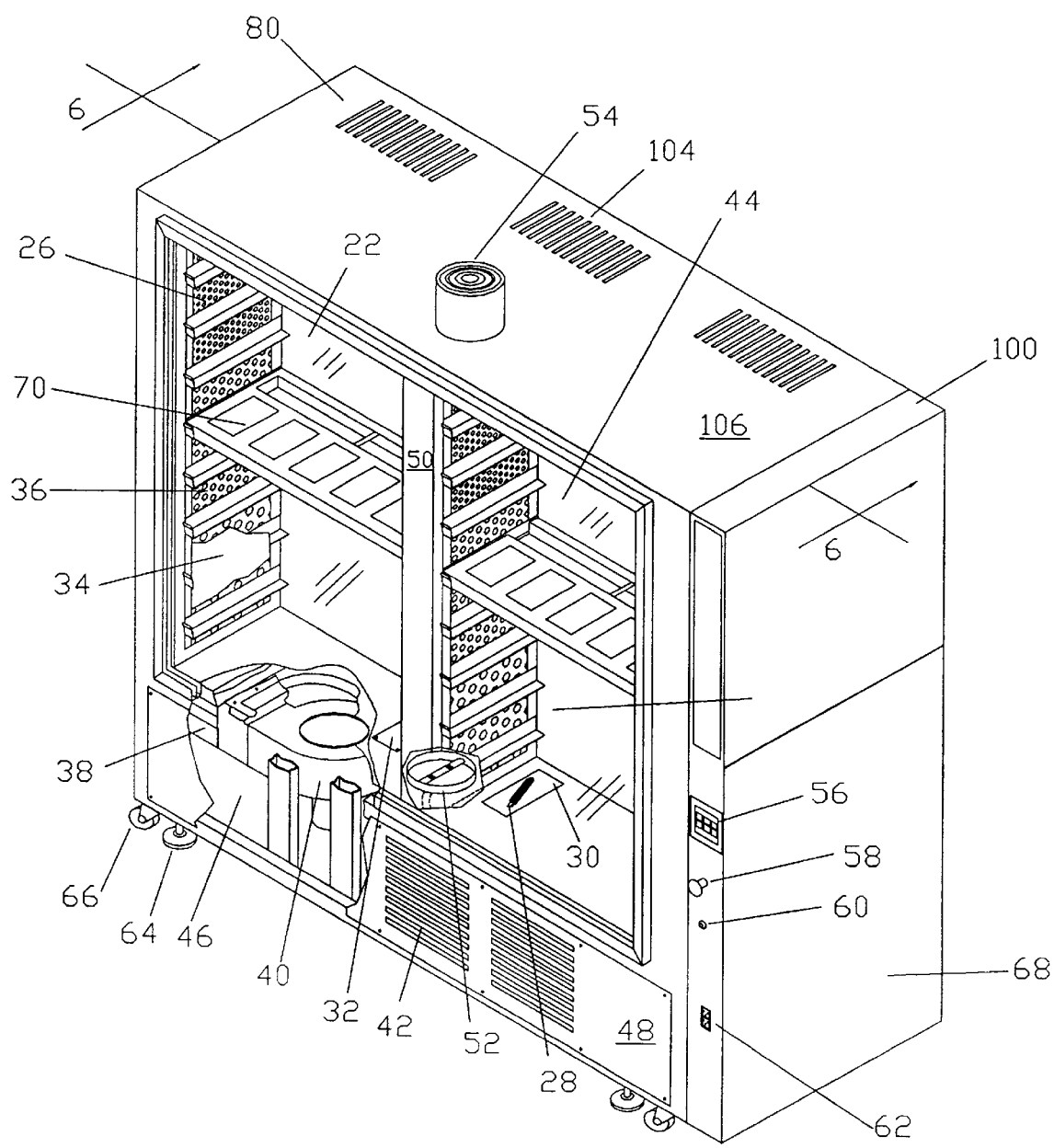
FIG. 1 is a pictorial diagram illustrating the overall environment of the disk drive tester of the first embodiment of the present invention.

FIG. 1 is a pictorial diagram illustrating the chamber for testing disk drives of the present invention, denoted generally by the numeral 20. The chamber 20 includes a left "Device Under Test" (DUT) bay 22 and a right DUT bay 24, brackets 26, heaters 28, heater housings 30, an access panel 32 to the heater housings 30, side air ducts 34, air duct cover panels 36, air duct transitions 38, pumps 40, front air intake vents 42, and sliding glass doors 44.

Additionally, the chamber 20 includes an appliance bay 46, a lower front panel 48, a central air duct 50, a motorized damper 52, an exhaust fan 54, a temperature display and controller 56, an emergency shutoff button 58, a master switch 60, electrostatic device (ESD) ground jacks 62, adjustable leveling feet 64, and casters 66.

Not shown in FIG. 1 is an electronics control bay 80 behind the DUT bays 22, 24 and a power bay 68 behind the lower right panel.

The chamber 20 is approximately six feet high, ten feet wide and four feet deep. The two DUT bays 22, 24 are housed in the upper front part of the chamber 20. The back part of the chamber 20 is the electronics control bay 80. Below the DUT bays 22, 24 is an appliance bay 46 which houses the pumps 40, air duct transitions 38, heater housings 30 and the motorized damper 52.

Parts related to one DUT bay are mirror images of the parts related to the other DUT bay. The left wall of the left DUT bay 22 is covered by a side air duct 34 and the right wall of the right DUT bay 24 is covered by a side air duct 34. Air duct cover panels 36 are attached over each of the side air ducts 34.

Each DUT bay employs a plurality of brackets 26 attached directly to the air duct cover panels 36 for supporting shelves 70 for holding the disk drives. Each DUT bay has a glass door 44. For access to one DUT bay, the glass door 44 slides in front of the other DUT bay.

Each DUT bay employs a heater 28 located in a heater housing 30 in the appliance bay 46. An access panel 32 to each heater housing 30 is in the floor of each DUT bay. Each DUT bay also employs a pump located in the appliance bay 46 for pumping air into the DUT bay. Each pump is connected to its respective side air duct 34 by an air duct transition 38.

The lower front panel 48 of the chamber 20 over the appliance bay 46 has front air intake vents 42 for providing access of fresh air into the appliance bay 46. The motorized damper 52 is attached under the central air duct 50 in the appliance bay 46. The motorized damper 52 draws in the fresh air from the front air intake vents 42 of the lower front panel 48 and sends it to the pumps 40. The fresh air is circulated in the DUT bays 22, 24 for assisting in maintaining the temperature inside the chamber 20 at the set point.

Between the two DUT bays 22, 24 is a central air duct 50. The central air duct 50 makes up the right wall of the left DUT bay 22 and the left wall of the right DUT bay 24. The sides of the central air duct 50 facing into the DUT bays 22, 24 are made similarly to the air duct cover panels 36 and also have brackets 26 for supporting the shelves 70.

On top of the chamber 20 and connected to the top of the central air duct 50 is an exhaust fan 54.

The lower panel on the right side of the chamber 20 covers a power bay 68 housing all electronic components of the invention. Electrically connected in the power bay 68 are the temperature controller 56, the emergency shutoff button 58, the master switch 60, and the ESD ground jacks 62 for discharging static electricity. The controller 56, emergency shutoff button 58, master switch 60, and ESD ground jacks 62 are located on the outside of the power bay 68 and on the lower right corner of the front of the chamber 20.

Under the chamber 20 are adjustable leveling feet 64 and casters 66.

Each DUT bay holds up to eight shelves 70. The shelves 70 are modular pieces that have a flexible configuration and can be constructed to the specifications required by the end user of the chamber 20. In the embodiment of FIG. 1, each shelf supports up to five 3½ inch disk drives.

In a preferred embodiment, the sliding glass doors 44 are tempered glass and are set in standard tracks. In one embodiment, the tracks are made of polypropylene and are commercially available.

There are four techniques employed in the present invention for decreasing vibration to the disk drives. One technique is to place vibration dampening materials on the brackets 26 where the shelves 70 will rest in such a way to protect the shelf from direct contact with the bracket, thereby minimizing vibration translation between the bracket and the shelf. Preferable vibration dampening materials for this purpose are self-adhesive neoprene foams, commercially available from Boyd Products. These vibration pads are purchased in sheets and cut down to the size of the brackets 26.

A second technique employed for vibration resistance in the present invention are neoprene pads on the adjustable leveling feet 64. The leveling feet 64 are commercially available and are rated at 400 lbs. each.

Preferable casters 66 are rated at 500 lbs. each and are available from Industrial Casters, Inc.

The tempered sliding glass doors 44, ESD ground jacks 62 and brackets 26 for the shelves 70 are standard in the art and are commercially available.

Figure 2:
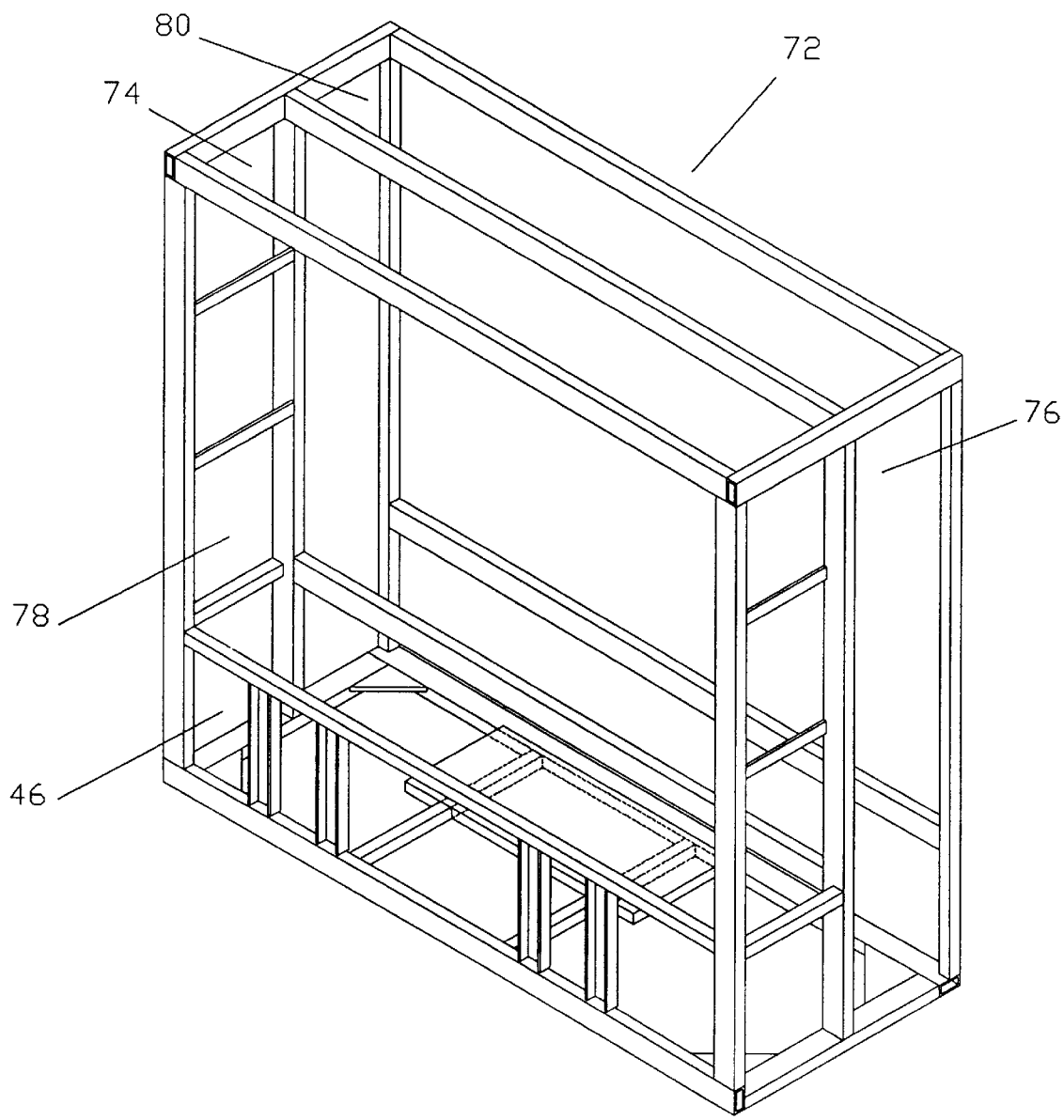
FIG. 2 is a pictorial diagram illustrating the frame of the present invention.

FIG. 2 illustrates the frame of the chamber 20 denoted generally by the number 72. Employment of a solid frame 72 is a third technique of vibration control in the present invention. The frame 72 is constructed of totally enclosed roll steel tubes. The frame 72 of FIG. 2 illustrates the upper front section 74 of the chamber 20 for housing the DUT bays 22, 24, the right and left sides of the DUT bays 76, 78 that will house the side air ducts 34, and the appliance bay 46 below the upper front section 74 of the chamber 20. The frame 72 also illustrates the electronics control bay 80 making up the back half of the invention.

The frame 72 is ordered and built to specifications from a machine shop. The frame 72 is painted and 24 gauge cold roll steel (CRS) is employed to complete the walls, ducts and various other parts of the chamber 20. The terms "sheet metal" and "steel" are used interchangeably and all are the same 24 gauge CRS which can be ordered to specifications from most sheet metal vendors. The sheet metal is attached on the inside and outside of the frame 72 for forming the top and bottom of the DUT bays 22, 24. A single sheet of CRS is placed on the outside of the right and left sides of the DUT bay. The lower front panel 48 and top panel 106 are ordered to specifications for crafting the air vents 42, 104.

The side walls and the top and bottom of the DUT bays 22, 24 are insulated to keep the temperature consistent in the DUT bays 22, 24 and keep the outer surfaces of the chamber 20 cool. Preferable thermal insulators for the DUT bays 22, 24 is a rigid fiberglass-type insulation, such as Celotex™ brand insulation, available from Celotex Manufacturing. The insulating material is placed between the two sets of sheet metal over the frame 72 of the top and bottom panels of the DUT bays 22, 24. The insulating material is placed between the side air duct 34 and the outer wall on the sides of the DUT bays 22, 24. The DUT bays 22, 24 are nearly airtight, maintaining an internal DUT dissipation of 5,000 watts or better. The tempered sliding glass doors 44 are not insulated.

Figure 3:
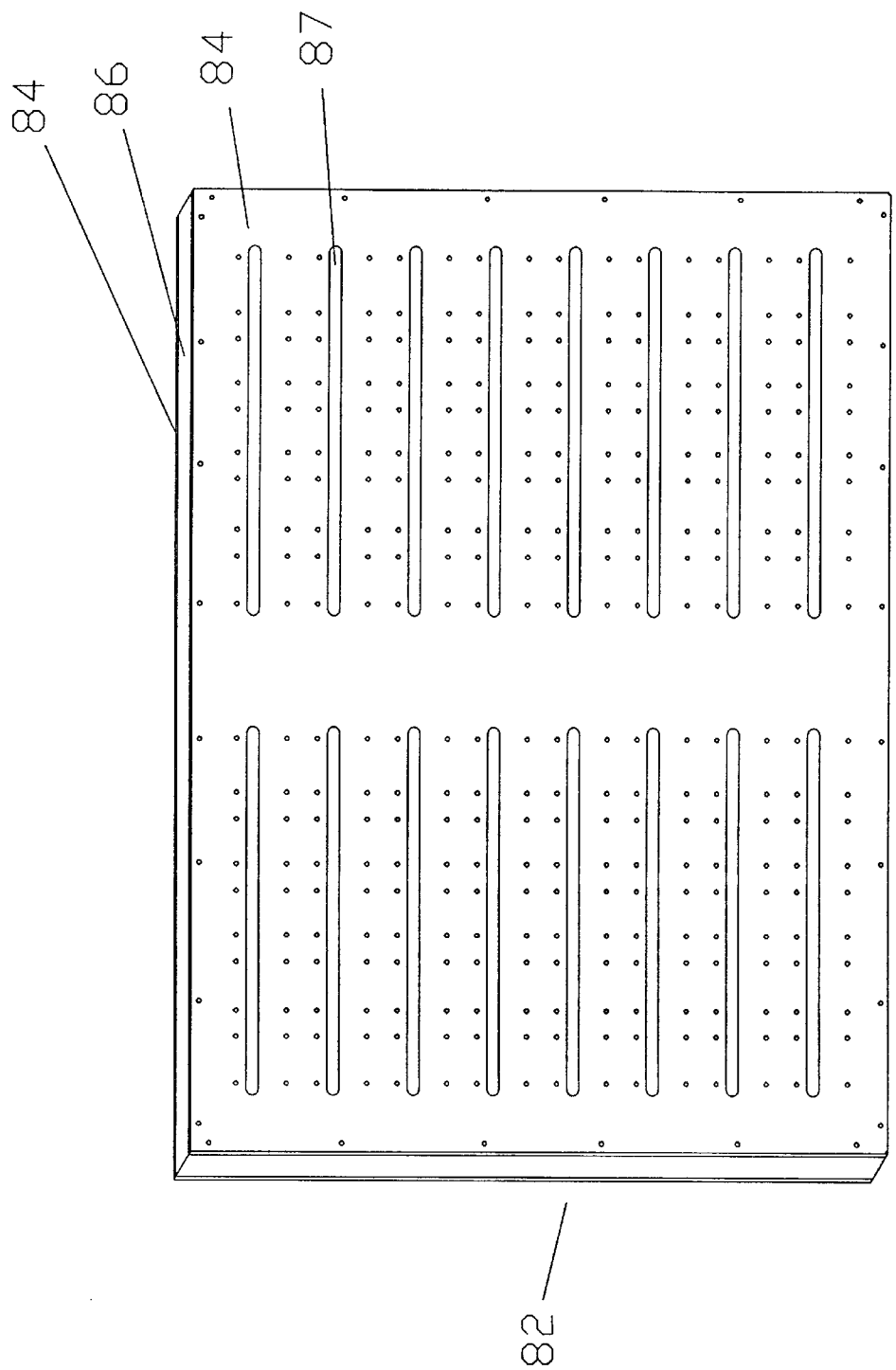
FIG. 3 is a pictorial diagram of the back wall of the DUT bays dividing the DUT bays from the electronics control bay of the present invention.

FIG. 3 illustrates the back wall of the DUT bays 22, 24 which divides the DUT bays and the electronics control bay 80, denoted generally by the numeral 82. The back wall 82 is also made of two sheets of steel 84 and is thermally insulated with a one inch closed cell anti-static foam 86. The slots 87 for electrical cables provide access from the electronics control bay 80 to inside the DUT bays 22, 24. Access through the insulation 86 is provided by making a fine, straight line cut through the insulation 86 at each slot 87. Such a cut in the insulation 86 is ordered from the vendor making the back wall 82 or can be made by an electric knife.

When the chamber 20 is complete the electronics control bay 80 is fully enclosed. The electronics control bay 80 houses electronics that the end user wishes to connect to the disk drives, for example, cables, wires, boards, or driver boards. The electronics control bay 80 also has adjustable brackets (not shown) on the right and left sides for supporting shelves for supporting the electronics. The electronics control bay 80 has two access doors in the back (not shown). The electronics control bay 80 is insulated from the temperatures inside the DUT bays 22, 24.

Figures 4, 5:
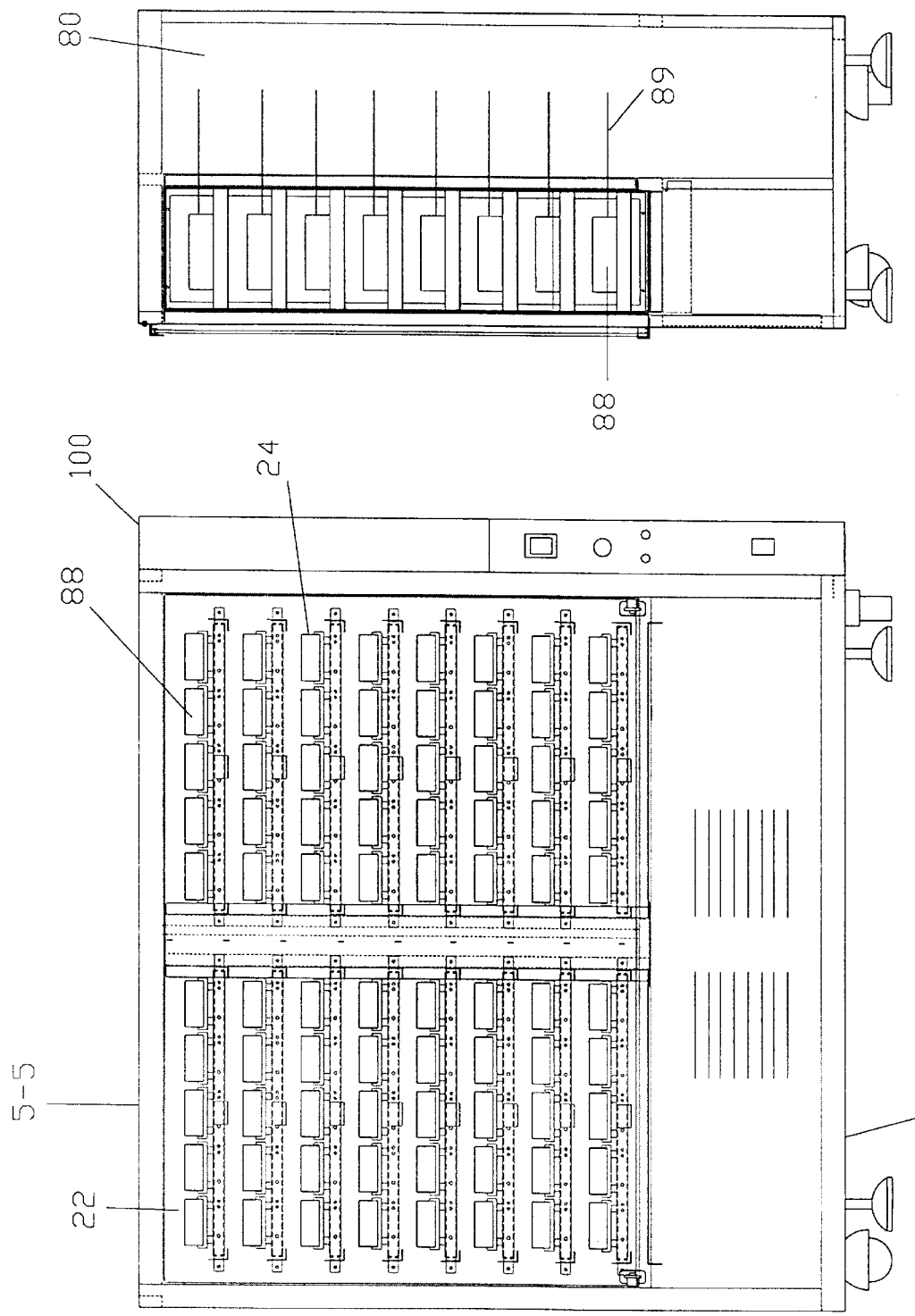
FIG. 4 is a view of the front of the chamber of the present invention being filled with disk drives.
FIG. 5 is a side view of the chamber through the line 5—5 of FIG. 4 illustrating the relationship between the front and back bays.

FIG. 4 is a front view of the chamber 20 showing the DUT bays 22, 24 filled with the maximum number of 3½ inch disk drives 88, visible through the tempered glass doors 44.

FIG. 5 is a cross sectional side view along line 5—5 of FIG. 4 illustrating the width of the DUT bays 22, 24 compared to the width of the electronics control bay 80, and illustrating electrical cables 89 entering the DUT bays 22, 24 through the slots 87.

Figure 6:
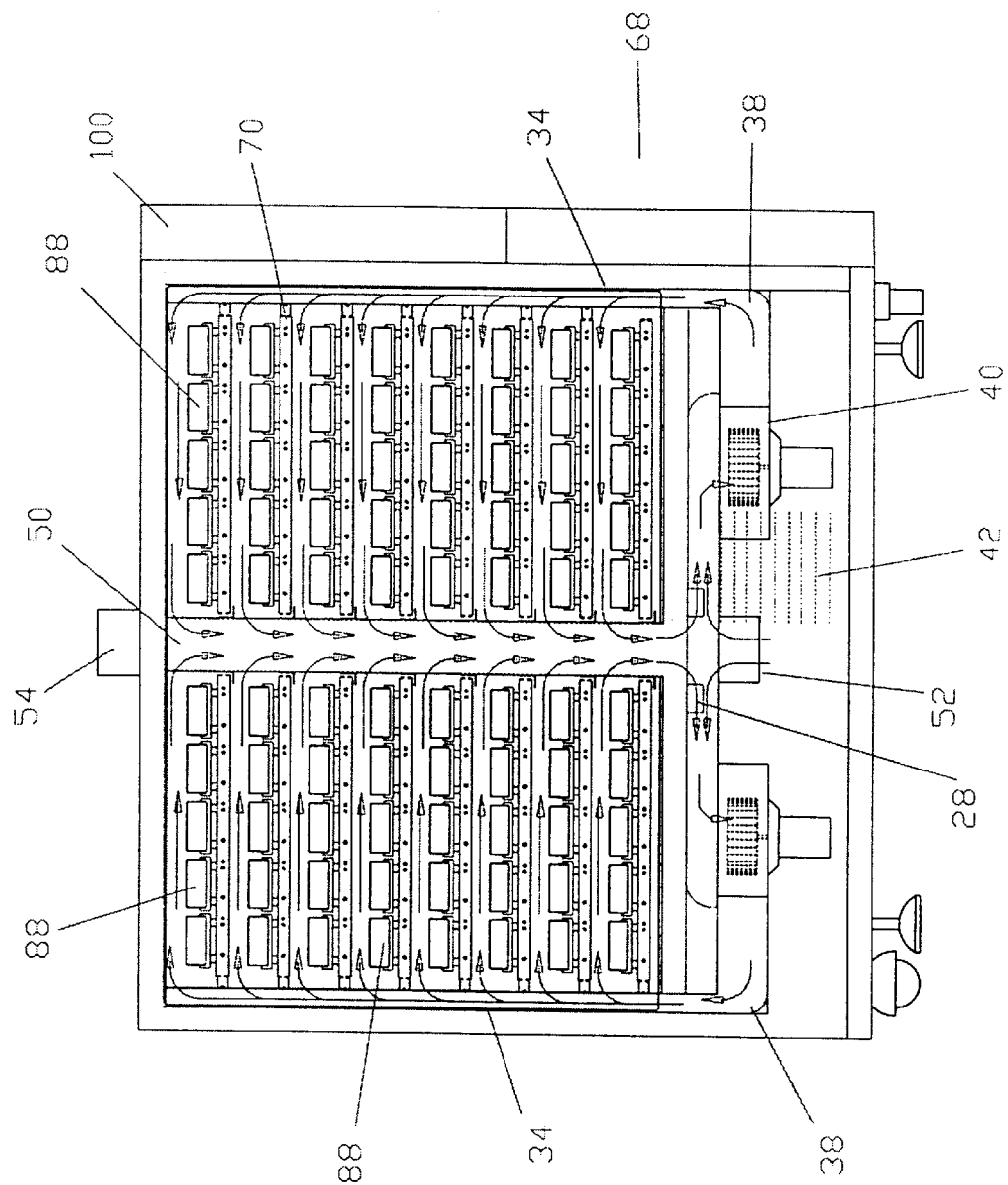
FIG. 6 is a cross-sectional view of the chamber employing arrows to illustrate the airflow within the chamber.

In FIG. 6 arrows illustrate the air flow pattern of the chamber 20 of the present invention along the line 6—6 of FIG. 1 when the chamber 20 is in typical operation. The heat control of the chamber 20 is maintained within 0.25° C. of the set point by employing the elements outlined in the darker lines of FIG. 6. The combination of elements highlighted includes the heaters 28, the pumps 40, the air duct transitions 38, the insulation of the DUT bay, precision air flow through the side 34 and central air ducts 50, fresh air intake by the motorized damper 52, and the exhaust fan 54.

In typical operation, the controller 56 is set at a desired temperature to simulate the actual working conditions of the disk drives 88. The master switch 60 is turned to the "on" position.

The temperature is then brought up to and maintained at the selected temperature by the controller 56 by circulating air in the closed loop system. A preferable controller 56 is front mounted and has user-friendly programming, for example, the Omega model #1120A, from Omega Manufacturing. A preferable controller 56 has a face which displays the temperature and allows for setting and changing the temperature.

The controller 56 activates the heaters 28 to heat the air in the DUT bays 22, 24 to the selected temperature. The two pumps 40 are turned on by the controller 56 to pump air through the air duct transitions 38 and up the side air ducts 34. Apertures in the air duct cover panels 36 release air across each shelf. The moving air then enters the apertures in the central air duct 50 and is guided back down to the heaters 28 and pumps 40.

Preferable pumps 40 are commercially available, 60 CFM ¼ horsepower air blowers from most electrical motor manufacturers.

A preferable heater 28 for heating the DUT bays 22, 24 is a commercially available resistive quick glow heater having a wattage above 5000 watts. Preferable heaters 28 are constructed of standard ceramic bars and a heater core for increasing the heating wattage and responding faster than heaters used in other systems. The heaters 28 generate heat to decrease the test time to simulate actual heat of running conditions. Therefore, the test will start one hour earlier in the present invention than in previous chambers.

Temperature sensors (not shown) are located in the lower part of the central air duct 50 to read the average temperature of the air coming from each shelf. The temperature sensors are electrically connected to the temperature controller 56.

When information is sent to the controller 56 by the sensors that the temperature of the air in the DUT bays 22, 24 approaches the selected temperature, the controller 56 turns on the motorized damper 52 and the exhaust fan 54. Fresh air is pulled in from the front air intake vents 42 by the motorized damper 52 and warm air is expelled through the exhaust fan 54. A preferable exhaust fan 54 is ordered from Dayton, Inc., model number 4C829A. Preferable motorized dampers 52 are made by Honeywell, Inc., model #1H805. With this air intake and exhaust mechanism in place, no cooling system is needed. The balance achieved by the heaters 28, air flow pattern and fresh air intake and warm air exhaust maintains the average temperature within the DUT bays 22, 24 to within ¼° C. of the selected temperature.

The chamber 20 has two safety features. First, the controller 56 will shut off the heating circuit if the temperature becomes 5° C. higher than the set point and will flash error signals that the heater 28 is disabled. A second safety feature is that the controller 56 will automatically shut off electrical power to the entire chamber 20 if the temperature becomes 7° C. higher than the set point in order to prevent the disk drives from generating additional heat.

The emergency shutoff button 58 (shown in FIG. 1) is useful for immediate manual shutdown of the system by disabling all power to the unit. The emergency button 58 is both easier and faster to utilize than the master switch 60. Immediate shut down may be desired in rare emergencies such as when the temperature exceeds the set point and the air intake and exhaust mechanism will not cool the DUT bays 22, 24 before damaging the drives, or when there is some type of electrical failure providing shocks or sparks. Preferable emergency buttons 58 are commercially available, for example, from Furnace Electrical Components.

Pumps 40, heaters 28 and controls operate at 208/240V AC, 50/60 Hz, 3 phase, 30A service. Power supplies operate at 110/220V AC.

Figure 8:
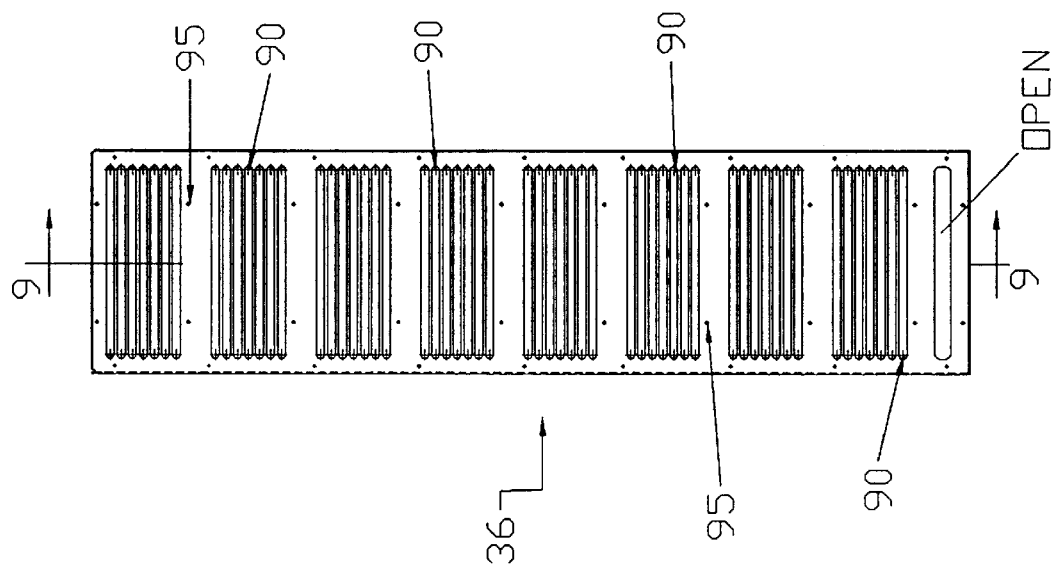
FIG. 8 is a front view of the air duct cover panels illustrating the elongated apertures on the outside of the air duct covers of the first embodiment of the invention.
Figure 7:
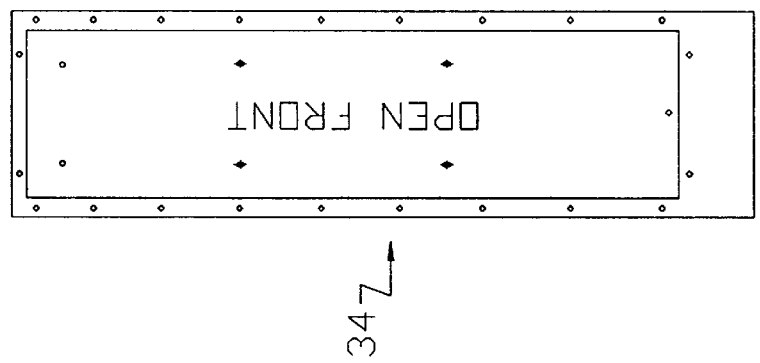
FIG. 7 is a front view of the side air ducts.

FIG. 7 is a front view of a side air duct 34. The side air ducts 34 are made of steel and are elongated tubes having an open front, an open bottom and a closed top. The air duct cover panels 36 of FIG. 8 are attached over the front opening of the side air ducts 34. Both of the side air ducts 34 and the air duct cover panels 36 are open at the bottom for allowing air to be pumped in by the pumps 40 through the air duct transition 38.

A critical aspect of the design of the invention is to ensure that an equivalent amount of air is circulated over each shelf. One method of providing equivalent air circulation is to have turning vanes attached to the back of the air duct cover panels 36 that faces inside the air duct 34 to divert the air over each shelf through identically sized apertures in the air duct cover panels 36. A second method is to have apertures of varying sizes in the air duct cover panels 36 without using turning vanes. The first method is preferred for mass production of the disk drive test chamber 20, however, each method diverts an equivalent air flow over each shelf.

In the first embodiment of the invention illustrated in FIGS. 1 and 8, the air duct cover panels 36 have elongated apertures 90. FIG. 8 illustrates the front of the air duct cover panels 36 which faces into the DUT bays 22, 24 when it is installed in the chamber 20. FIG. 9 is a side view of the combined side air duct 34 and air duct cover panel 36 through the line 9—9 of FIG. 8. The backs of the air duct cover panels 36 facing the inside of the side air ducts 34 have turning vanes 92 for diverting equivalent amounts of air pumped into the side air ducts 34 across each shelf 70 in the DUT bays 22, 24. The pattern of apertures 90 are equivalent on each of the right and left air duct cover panels 36 and on both sides of the walls of the central air duct 50 facing the inside of the DUT bays 22, 24.

As air is pumped into the side air ducts 34, the air flow velocity causes air pressure to be higher near the top of the side air duct 34 than near the bottom. Therefore, the turning vanes on the back of the air duct cover panels 36 are shorter near the top of the air duct and longer near the bottom. Longer lengths of turning vanes will give more air flow near the bottoms of the DUT bays 22, 24, thus equalizing the pressure of air leaving each set of apertures over each shelf. The length (i.e., dimension "A" in FIG. 11) of the lower lip of the turning vane is 0.33 inches nearest the top. The lengths "A" of the lower lip of each turning vane gradually increase as the vanes near the bottom of the air duct. The next lengths "A" are 0.5 inch, 0.75 inch and 1.0 inch, respectively. The specific angle of the bend in the turning vanes is 45°. This angle also directs the air flow equivalently over each disk drive. These numbers were arrived at empirically by considerations of air flow dynamics.

The gaps between the apertures are placed where the turning vanes and the shelves 70 will rest. The arrows illustrate the direction of air flow through the turning vanes as it exits through the elongated perforations over the shelves 70.

FIG. 10 is a front view of the turning vanes 92. Attachments 94 correspond to the attachment points 95 in FIG. 8.

FIG. 11 is a side view of the turning vane of FIG. 10 through line 11—11 further illustrating the angle and length "A" of the turning vanes of the present invention.

The central air duct 50, illustrated in FIGS. 1, 4, 6 and 12, divides the DUT bay into two halves. The central air duct 50 helps keep the temperature equivalent on each disk drive because it increases precision air flow on each shelf. Therefore, any combination of partial loading of disk drives into the DUT bays 22, 24 will get even temperature airflow.

The central air duct 50 is rectangular. The two opposing sides facing the DUT bays 22, 24 are an air duct cover panel 36 and a modified air duct cover panel 36. The modified air duct cover panel 36 has a 90 degree angled sheet of steel for providing a third side 98 of the central air duct 50. The fourth side of the central air duct 50, opposite the third side 98, is the back wall 82 of the DUT bays 22, 24.

Figure 12:
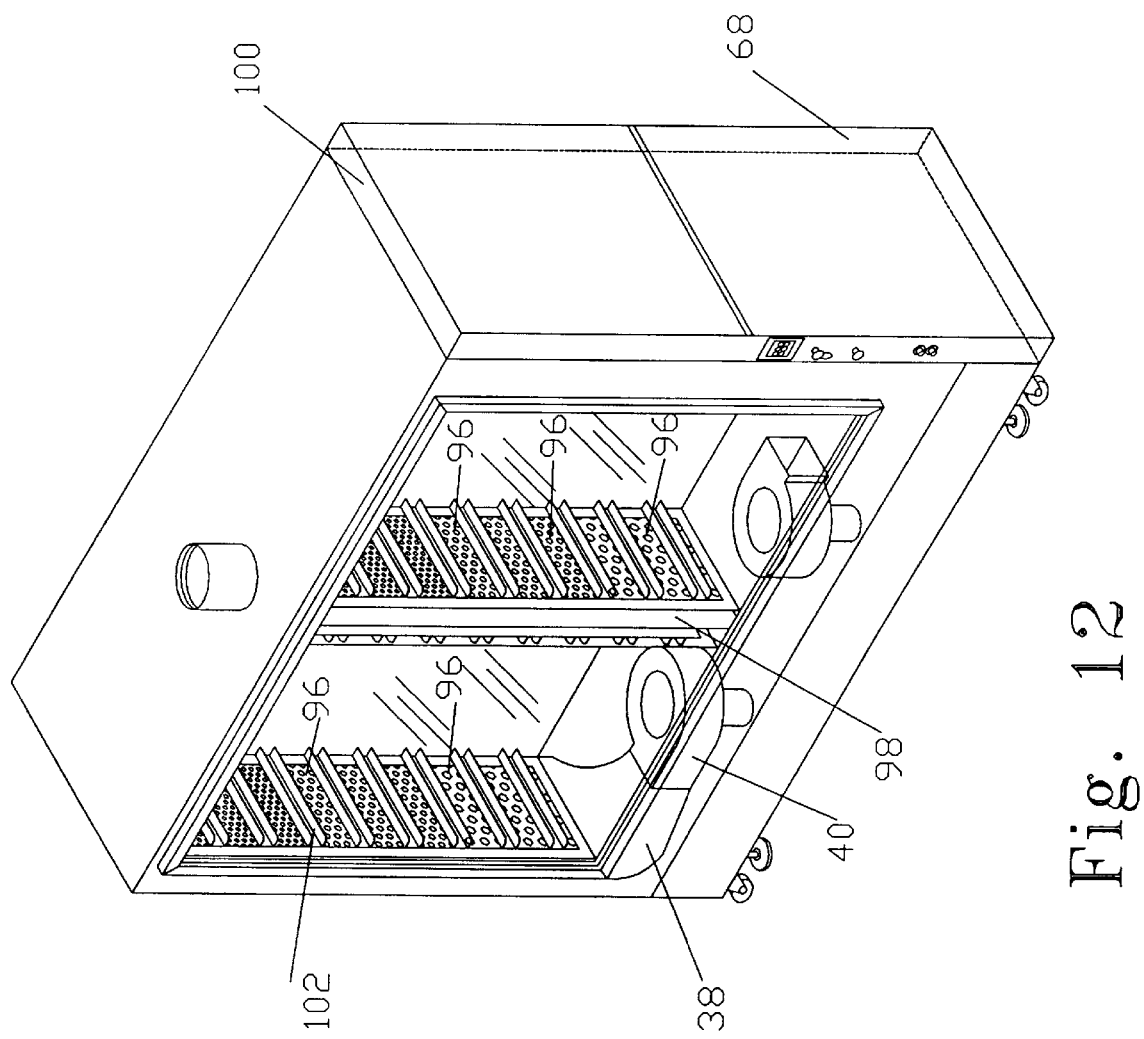
FIG. 12 pictorial diagram illustrating the perforated air duct cover panels of the second embodiment of the present invention.

FIG. 12 also illustrates a second embodiment of the invention having varying sized circular apertures 96 in the air duct cover panels 36 as opposed to the elongated apertures 90. Additionally, the second embodiment does not employ turning vanes for releasing equivalent amounts of air flow across each shelf. Instead, the size of the apertures 96 are varied for providing equivalent amounts of air flow to each of the shelves 70 in the DUT bays 22, 24. The patterns of apertures 96 on the air duct cover panels 36 of the right and left side air ducts 34 and on both sides of the walls of the central air duct 50 facing the inside of the DUT bays 22, 24 are equivalent. Each side of an air duct that faces the inside of a DUT bay has large apertures 96 near the bottom of the DUT bay and smaller apertures 96 near the top of the DUT bay. Larger apertures 96 near the bottom have a similar effect of equalizing the pressure of air leaving each set of apertures 96 over each shelf 70, as do the longer turning vanes 92 in the first embodiment.

There are three sizes of apertures 96. The net percentage of opening per square inch of air duct cover panel 36 is 70 percent open near the bottom, 50 percent open near the center and 40 percent open near the top. These numbers are arrived at empirically by considerations of pump output, size of doc works, and air flow dynamics.

The apertures 96 are in nine sections with solid areas between each section. The air duct covers have tracks 102 over these solid areas for sliding the shelves 70 into the DUT bays 22, 24.

FIG. 12 also illustrates the relationship of the air duct transitions 38 to the pumps 40 and the attachment of the power bay 68 to the rest of the chamber 20.

The power bay 68 is thermally isolated from the DUT bays 22, 24. Contained in the power bay 68 are two safeties and all associated electrical components of the chamber 20 for facilitating maintenance and trouble shooting. Additional side panels 100 added to the right side of the frame 72 of the chamber 20 are illustrated in FIGS. 1, 4, 6, 12. These extra side panels 100 add less than five inches of width to the chamber 20 to accommodate the power bay 68.

Figure 13:
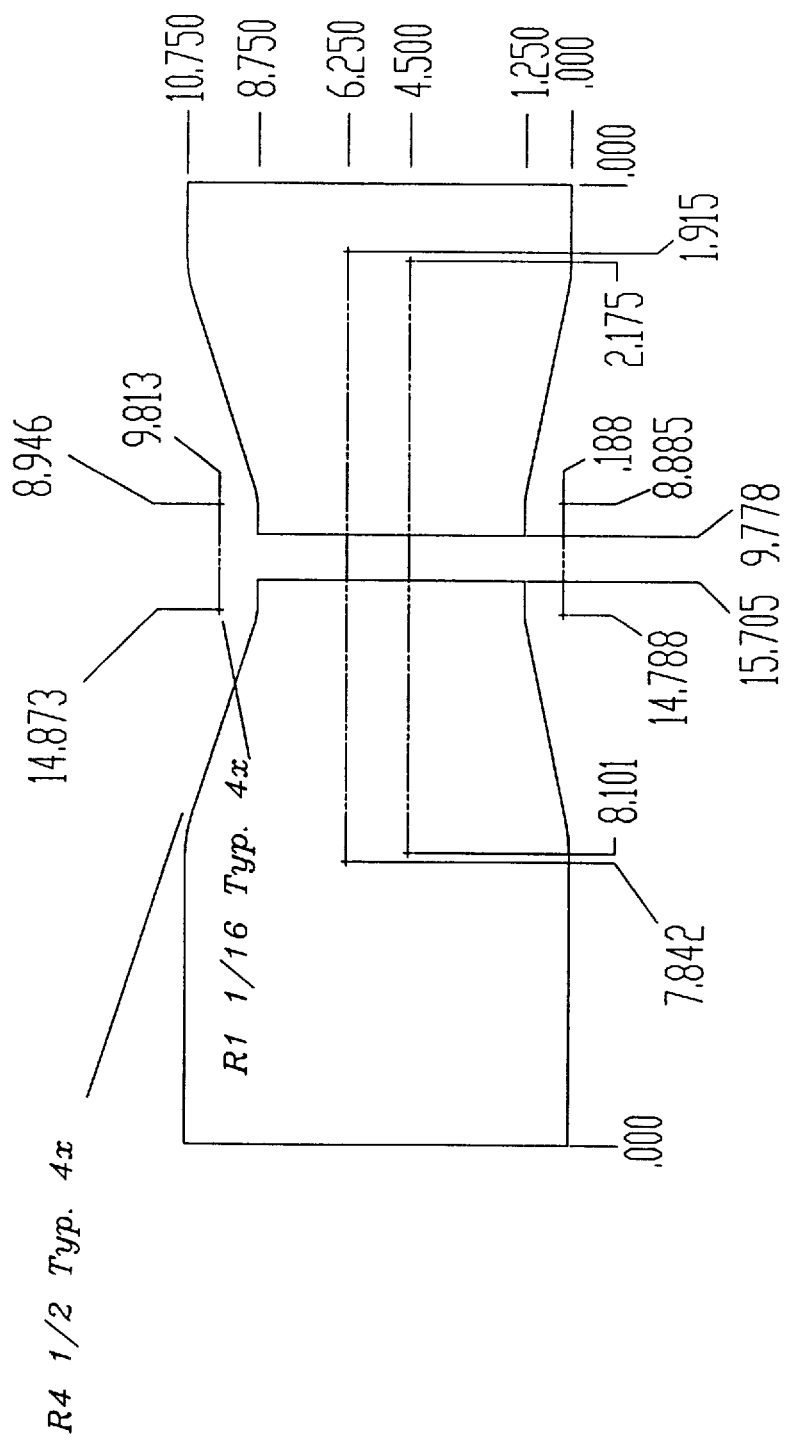
FIG. 13 is a schematic for making the air duct transition that joins the pump and side air duct.

FIG. 13 is a pictorial view of the air duct transitions 38. The air duct transition 38 is made of well-known, high density, high temperature resistant rubber, for example, EPDM (ethylene-propylene terpolymer), which is also used for automotive parts, cable coating, hose, footwear, and other products. The air duct transition 38 can be ordered to specifications from most plastics molding companies or the rubber can be ordered in sheets, and formed into a hollow connection.

The air duct transitions 38 include a fourth technique employed in the present invention for decreasing translation of the mechanical vibrations of the pump motor 40 to the side air ducts 34 and onto the shelves 70. The transition air ducts 38 have vibration dampening pads on the inlet of the blower to absorb the mechanical vibrations from the pump so that it is not transferred to the air ducts. Alternatively, a one inch closed cell anti-static foam is attached on the air duct transition 38 between the air duct transition 38 and the pump 40.

Figure 14:
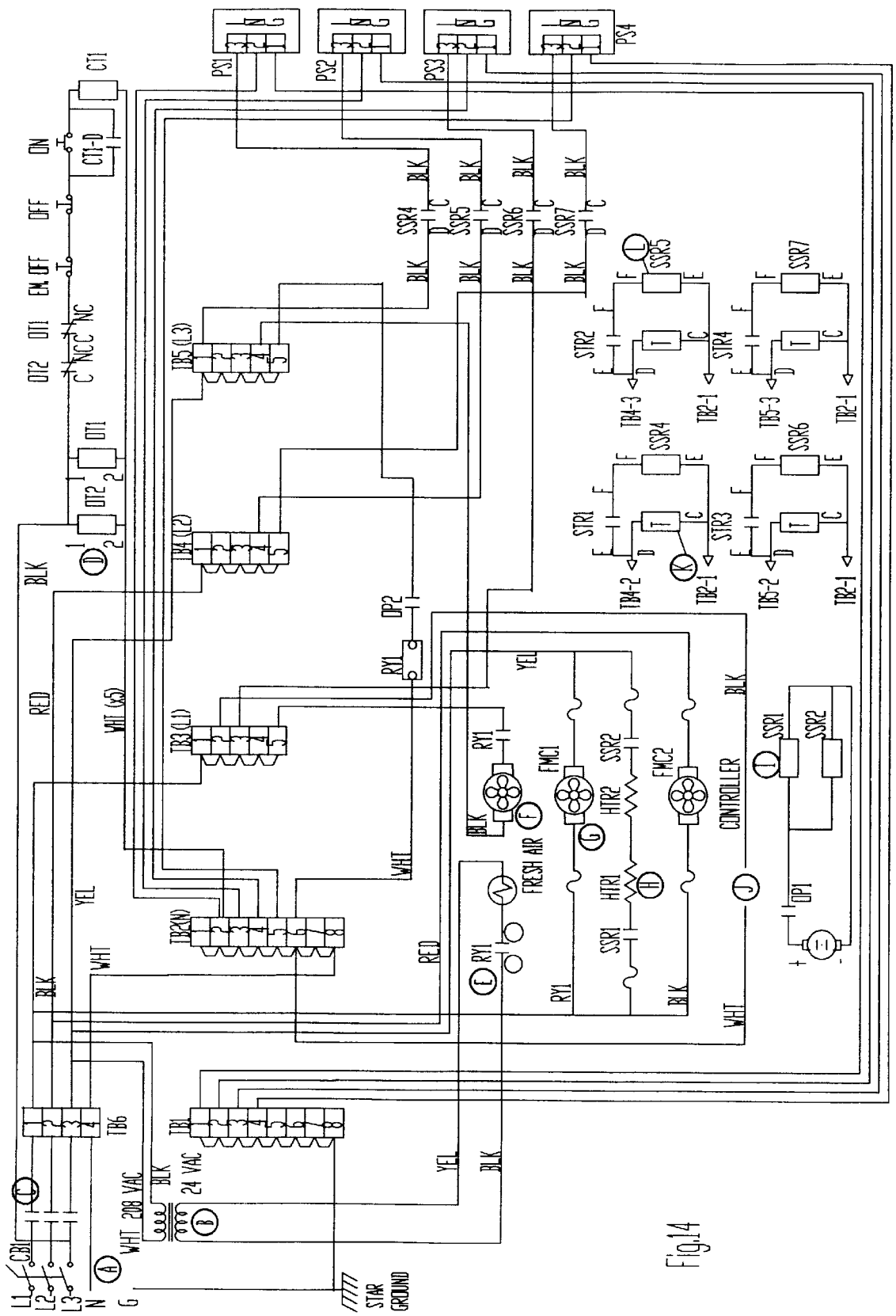
FIG. 14 is a schematic of the wiring diagram for the present invention.

FIG. 14 is a schematic of the wiring diagram for the electrical components found in the power bay 68 beneath the lower right panel. Wiring of each of the electrical components to the controller 56 is accomplished through routine procedures.

In an alternative embodiment the chamber 20 has a mounting area for a host computer, a host computer flat panel display to electronics control bay, a hideaway host computer keyboard tray, and cable feed-through holes for cables from the front panel controls. The DUT bays 22, 24 are interfaced into the host computer for obtaining the pass rate of every drive. The software of the host computer can give reasons for drive failure and give information regarding the adequacy of electrical connections for each drive. This interface is especially helpful if a company is testing several thousand disk drives at a time.

While the foregoing detailed description has described a first embodiments of the disk drive test chamber in accordance with this invention, it is to be understood that the above description is illustrative only and not limiting of the disclosed invention. Thus the invention is to be limited only by the claims as set forth below.

What is claimed is:

1. A device for testing disk drives comprising:

a test bay having a right side, a left side, a ceiling and a floor, the test bay being adapted for housing a plurality of shelves for holding a plurality of disk drives in the test bay, and the test bay being maintainable in a predetermined temperature range;

at least one heater located below the test bay for heating the test bay;

a left air duct and a right air duct positioned on the right and left sides of the test bay for supplying air in an upward direction, the left and right air ducts having air duct covers;

at least one pump for pumping air up the left and right air ducts;

a central air duct located in the center of the test, the central air duct extending from the floor of the test bay to the ceiling of the test bay and separating the test bay into a right half and a left half, the central air duct being for returning the supply of the air in a downward direction toward the pump, the central air duct having at least one central air duct cover;

the left air duct, the right air duct and the central air duct each having a hollow interior with a plurality of turning vanes positioned in the hollow interior for balancing the air flow to various regions of the test bay;

a front lower panel positioned below the test bay and including at least one air intake vent;

a motorized damper positioned below the test bay for drawing in air through the air intake vent;

an exhaust fan positioned on the test bay for expelling air from inside the test bay; and perforations in the air duct covers of the left and right air ducts and equivalent perforations in the central air duct cover for balancing air flow to various regions inside the test bay.

2. The device according to claim 1 further comprising thermal insulation in the test bay for improving temperature control.

3. The device according to claim 1 wherein the predetermined temperature range is within ¼° C. of a set point, the set point being within the range of room temperature to 75° C.

4. The device according to claim 1 wherein the air duct covers and the central air duct cover have brackets for supporting a plurality of shelves and vibration dampening pads attached to the brackets for minimizing the contact between the brackets and the shelves.

5. The device according to claim 1 further comprising an air duct transition connecting the pump and the left air duct for transferring air from the pump to the left air duct, the point of connection of the air duct transition to the pump having a vibration dampening pad for minimizing translation of the vibration from the pump to the left air duct.

6. The device according to claim 1 further comprising leveling feet for leveling the device, the leveling feet having vibration dampening pads for minimizing vibration translation from the floor of the room containing the device to the device.

7. The device according to claim 3 wherein all power to the device shuts down when the temperature of the test bay is 7° C. higher than the set point.

8. The device according to claim 1 further comprising a controller that activates and deactivates the heater and the pump.

* * * * *